US00PP30579P2

(12) United States Plant Patent
van Nijnatten

(10) Patent No.: US PP30,579 P2
(45) Date of Patent: Jun. 18, 2019

(54) ***ILEX* PLANT NAMED 'ANNYS DWARF'**

(50) Latin Name: ***Ilex* x *meserveae***
Varietal Denomination: Annys Dwarf

(71) Applicant: André van Nijnatten, Zundert (NL)

(72) Inventor: André van Nijnatten, Zundert (NL)

( * ) Notice: Subject to any disclaimer, the term of this patent is extended or adjusted under 35 U.S.C. 154(b) by 0 days.

(21) Appl. No.: 15/732,663

(22) Filed: Dec. 11, 2017

(51) Int. Cl.
*A01H 5/12* (2018.01)

(52) U.S. Cl.
USPC ..... Plt./247
CPC ..... *A01H 5/12* (2013.01)

(58) Field of Classification Search
USPC ..... Plt./247
See application file for complete search history.

*Primary Examiner* — Anne Marie Grunberg
(74) *Attorney, Agent, or Firm* — Penny J. Aguirre

(57) ABSTRACT

A new cultivar of *Ilex* x *meserveae* plant named 'Annys Dwarf' that is characterized by its foliage that is fine, glossy and dark green in color and changing to dark purple-green in winter, its abundant flowering in the spring, its exhibits a compact plant habit, its lack of berry production (male flowers), and its leaf surfaces that smooth with spines on margins that are soft and not prickly.

2 Drawing Sheets

Botanical classification: *Ilex* x *meserveae*.
Variety denomination: 'Annys Dwarf'.

CROSS REFERENCE TO A RELATED APPLICATION

This application is related to a European plant breeders' rights application filed on Feb. 14, 2016, application No. 2016/0499. There have been no offers for sale anywhere in the world more than one year prior to the filing of this Application and no accessibility to one of ordinary skill in the art could have been derived from the printed plant breeder's rights documents.

BACKGROUND OF THE INVENTION

The present invention relates to a new and distinct cultivar of *Ilex* x *meserveae* and will be referred to hereafter by its cultivar name, 'Annys Dwarf'. 'Annys Dwarf' is a new cultivar of Meserve hybrid holly grown for use as an ornamental landscape plant.

'Annys Dwarf' was discovered by the Inventor as a chance seedling in a trial field in Zundert, The Netherlands in 2006. The parentage is unknown.

Asexual propagation of the new cultivar was first accomplished by one of the Inventors using semi-hardwood stem cuttings in October of 2010 in Zundert, The Netherlands. Asexual propagation by semi-hardwood stem cuttings has determined that the characteristics of the new cultivar are stable and are reproduced true to type in successive generations.

SUMMARY OF THE INVENTION

The following traits have been observed repeatedly and represent the characteristics of the new cultivar. These attributes in combination distinguish 'Annys Dwarf' as a unique cultivar of *Ilex*.

1. 'Annys Dwarf' exhibits foliage that is fine, glossy and dark green in color and changing to dark purple-green in winter.
2. 'Annys Dwarf' exhibits abundant flowering in the spring.
3. 'Annys Dwarf' exhibits a compact plant habit.
4. 'Annys Dwarf' exhibits no berry production (male flowers).
5. 'Annys Dwarf' exhibits leaf surfaces that smooth with spines on margins that are soft and not prickly.

'Annys Dwarf' can be most closely compared to the *Ilex* x *meserveae* cultivars 'Blue Prince' (not patented) and 'Geers' (U.S. Plant Pat. No. 27,755). 'Blue Prince' is similar to 'Annys Dwarf' in having dark green foliage. 'Blue Prince' differs from 'Annys Dwarf' in having a taller plant height and foliage that stays dark green in winter. 'Geers' is similar to 'Annys Dwarf' in having leaf margins that are soft and not prickly. 'Geers' differs from 'Annys Dwarf' in having variegated foliage.

BRIEF DESCRIPTION OF THE DRAWINGS

The accompanying colored photographs illustrate the overall appearance and distinct characteristics of a three year-old plant of the new cultivar as grown outdoors in a 23-cm container in Boskoop, The Netherlands.

The photograph in FIG. 1 provides a side view of the plant habit of 'Annys Dwarf'.

Figure 1:
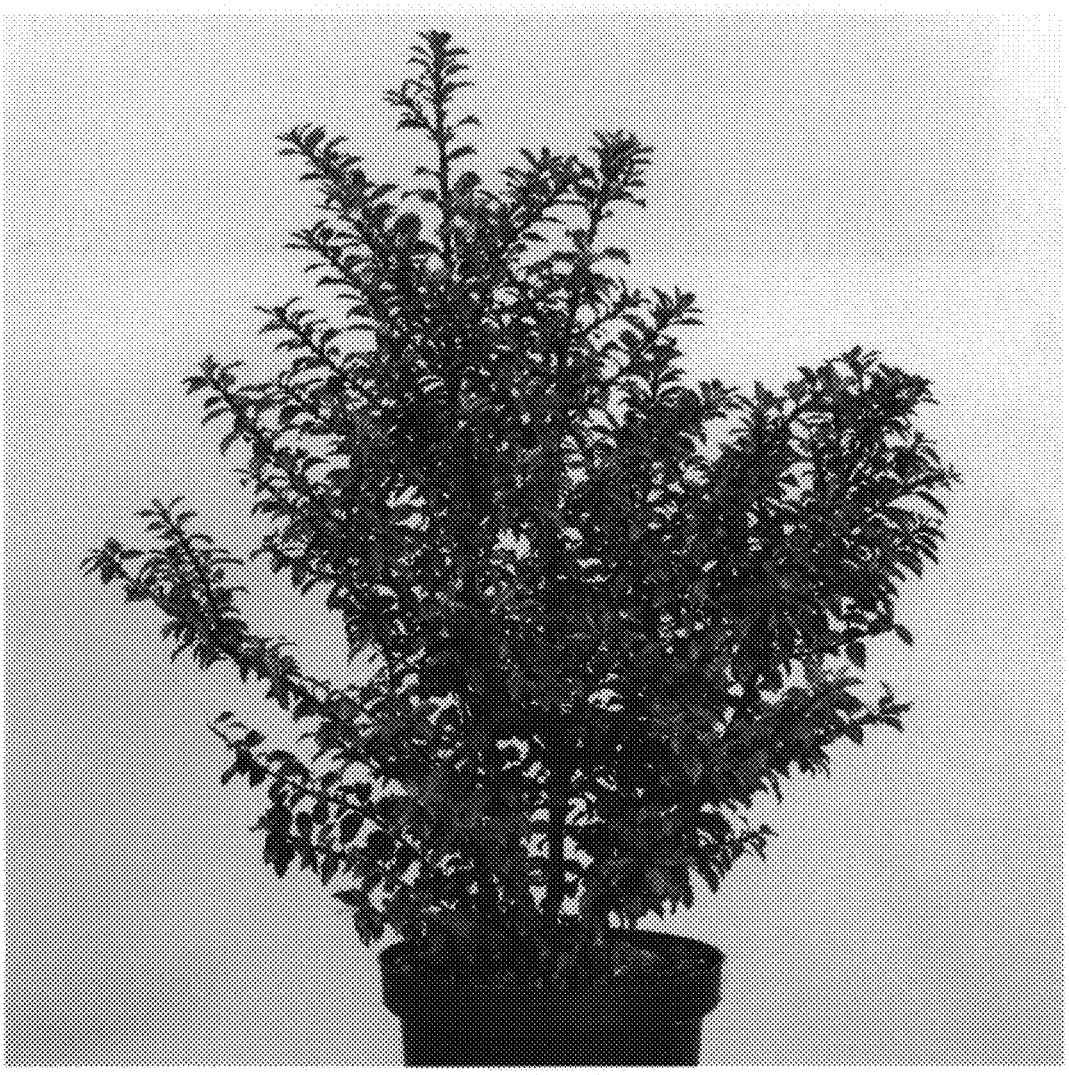
Figure 2:
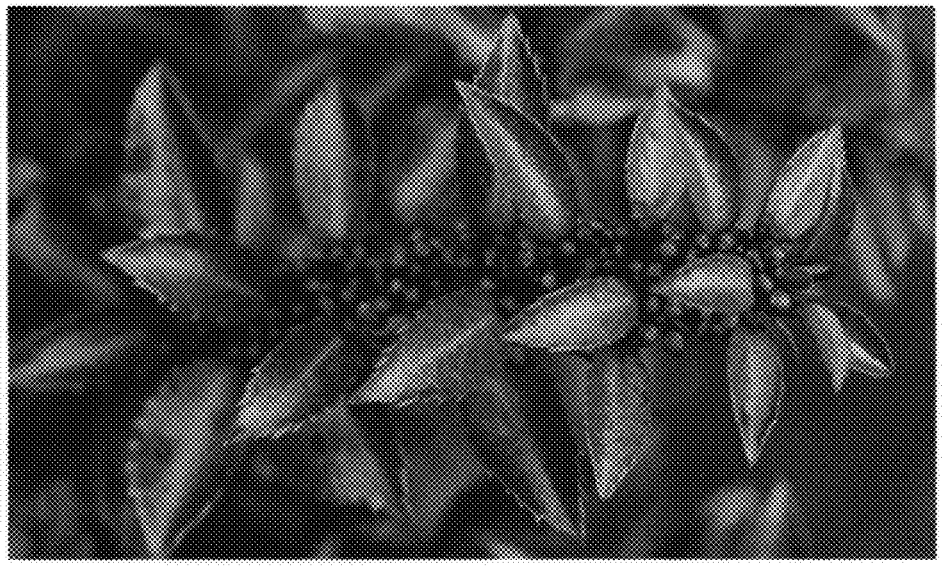

The photograph in FIG. 2 provides a close-up view of flower buds and foliage of 'Annys Dwarf'.

Figure 3:
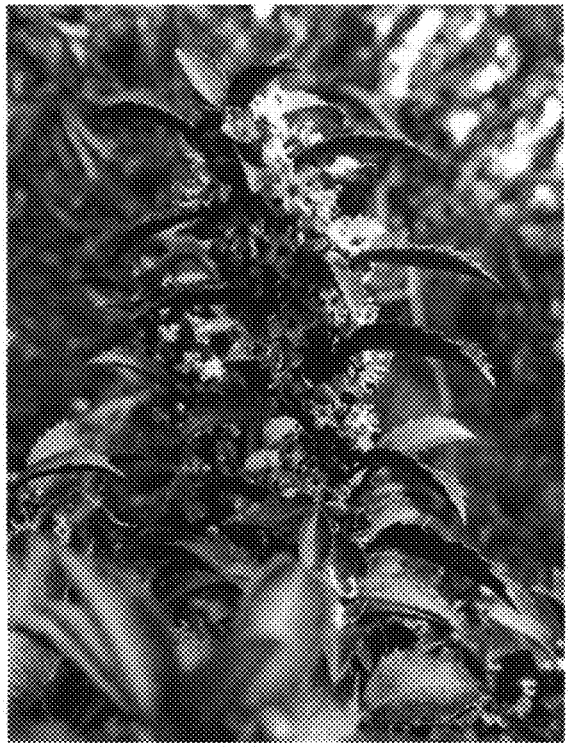

The photograph in FIG. 3 provides a close-up view of the flowers of 'Annys Dwarf'.

The colors in the photographs may differ slightly from the color values cited in the detailed botanical description, which accurately describe the colors of the new *Ilex*.

DETAILED BOTANICAL DESCRIPTION

The following is a detailed description of three-year-old plants of the new cultivar grown outdoors in 23-cm containers in Boskoop, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—March to May in The Netherlands.

*Plant type.*—Evergreen, perennial shrub.

*Plant habit.*—Broadly spreading, upright, broad ovate in shape.

*Height and spread.*—Reaches an average of 70 cm in height and 50 cm in width.

*Hardiness.*—At least in U.S.D.A Zones 6 to 10.

*Diseases and pests.*—No susceptibility to diseases has been observed.

*Root description.*—Densely fibrous and 165C in color.

*Propagation.*—Semi-hardwood stem cuttings.

*Root development.*—Cuttings root in 2 to 3 months in fall in a plug, plugs planted in a P9 container will fully root by the following fall.

*Growth rate.*—Moderate.

Branch description:

*Branching.*—Freely branching; 5 main branches each with an average of 52 lateral branches per main branch.

*Stem size.*—Main branches; an average of 65 cm in height, lateral branches; an average of 22.8 cm in length, 3 mm in diameter.

*Stem surface.*—Glabrous and matte.

*Stem shape.*—Pentagonal.

*Stem aspect.*—Lateral branches in an average angle of 45° to main branches.

*Stem strength.*—Very strong.

*Stem color.*—Young stems; upper side N200A, lower side 146C, mature stems; upper side 202A and tinged 147A and N200A, lower side 148A.

*Internode length.*—Average of 5 mm.

Foliage description:

*Leaf shape.*—Ovate.

*Leaf division.*—Simple.

*Leaf base.*—Cuneate.

*Leaf apex.*—Acute.

*Leaf fragrance.*—None.

*Leaf venation.*—Pinnate, upper surface veins 143C, lower surface veins 144C.

*Leaf margins.*—Serrate with soft spines.

*Leaf arrangement.*—Alternate.

*Leaf aspect.*—Moderately to strongly undulate.

*Leaf attachment.*—Petiolate.

*Leaf surface.*—Both surfaces smooth, glabrous, non-rugose, slightly glossy.

*Leaf size.*—Mature and young leaves; 3.1 cm in length, 1.7 cm in width.

*Leaf quantity.*—Average of 45 per lateral branch.

*Leaf color.*—Young leaves upper surface; between 141A and 146A with slight markings of N186A, young leaves lower surface; 143B, mature and fall leaves upper surface; a color between 139A and 147A with slight markings of N186A, mature and fall leaves lower surface; 146B to 146C, winter bot hsurfaces; become suffused with N186A.

*Petioles.*—Average of 5.5 mm in length, 1.5 mm in diameter, strong, smooth and glabrous surface, upper surface color N199B, lower surface color 144B.

Flower description:

*Inflorescence type.*—Clusters of male flowers at axils of lateral branches.

*Inflorescence.*—Clustered axillary cyme, an average of 1.5 cm in height, 1.3 cm in diameter.

*Lastingness of flowers.*—Average of 7 days persistent, self-cleaning.

*Flower size.*—An average of 8 mm in height and width, 6 mm in depth.

*Flower fragrance.*—None.

*Flower number.*—An average of 12 flowers per cluster, 200 flowers per plant.

*Flower aspect.*—Upright to outward.

*Flower type.*—Rotate, single, extemely free.

*Flower buds.*—Obovate in shape, smooth, glabrous and matte surface, an average of 3 mm in length and 2 mm in width, color; N81A and becoming 145C to 145D with apex tinged with 180D prior to opening, sepals portion 200B, tinged 144A towards the base.

*Petals.*—4 to occasionally 5, broad oblong, slightly concave in shape, base fused, glabrous, slightly velvety and very slightly glossy, entire magins, when opening and fully open upper and lower surface NN155D, slightly tinged at the top N77B.

*Calyx.*—Rotate, cup-shaped, 1.5 mm in length, 2 mm in diameter.

*Sepal.*—Rotate, 4 to occasionally 5, an average of 1.5 mm in length and 1.25 mm in width, broad ovate in shape, entire margin, broad cuneate base, upper and lower surface smooth, glabrous, matte, color; when opening and fully open upper surface 200B to 200C and tinged towards the base 144B, when opening and fully open lower surface 200B and tinged towards the base 144A.

*Peduncle.*—Round in shape, an average of 3 mm in length, 1 mm in diameter, held in an average angle of 55°, moderately strong, smooth and glabrous surface, color between N186C and 200A.

*Pedicel.*—Round in shape, an average of 4 mm in length, 0.75 mm in diameter, held in an average angle of 30°, moderately strong, smooth and glabrous surface, color 199A.

Reproductive organs:

*Gynoecium.*—None present, monoecious, ovary not developed, 146A in color.

*Androecium.*—Stamens; 4, filaments; 4 mm in length, NN155D in color, anther; short oblong in shape, 0.1 mm in length, 0.75 mm in width, 202A in color, pollen; high in quantity, 4B in color.

*Fruit/seeds.*—None produced, no female flowers are produced.

It is claimed:

1. A new and distinct cultivar of *Ilex* plant named 'Annys Dwarf' as herein illustrated and described.

* * * * *